United States Patent [19]

Reiter

[11] Patent Number: 4,482,723
[45] Date of Patent: Nov. 13, 1984

[54] PROCESS FOR PREPARATION OF 4-ACETYL-2-SUBSTITUTED-IMIDAZOLES

[75] Inventor: Lawrence A. Reiter, Gales Ferry, Conn.

[73] Assignee: Pfizer Inc., New York, N.Y.

[21] Appl. No.: 483,787

[22] Filed: Apr. 11, 1983

[51] Int. Cl.³ .......................................... C07D 233/64
[52] U.S. Cl. .................................................. 548/343
[58] Field of Search ........................................ 548/343

[56] References Cited

U.S. PATENT DOCUMENTS 4,374,843  2/1983  LaMattina et al. ................ 424/270

OTHER PUBLICATIONS

Catch et al., J. Chem. Soc., (London), 278, (1948).
McLamore et al., J. Org. Chem., 20, 109, (1955).
Petrov, Chem. Abstr., 38, 1467⁴, (1944).

Primary Examiner—Robert W. Ramsuer
Attorney, Agent, or Firm—Charles J. Knuth; Albert E. Frost; Paul D. Thomas

[57] ABSTRACT

Novel intermediates of the formula

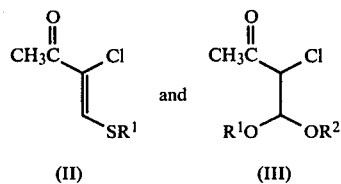

where $R^1$ and $R^2$ are each $(C_1-C_4)$alkyl or taken together are $(C_2-C_4)$alkylene, and their use in a process for preparation of compounds of the formula

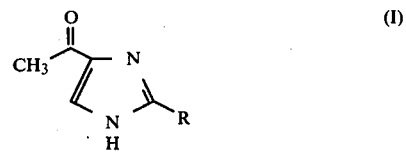

where R is $(C_1-C_6)$alkyl or $(CH_2)_n Ar$, Ar is phenyl or phenyl monosubstituted by Cl, Br, F, $CH_3$ or $OCH_3$ and n is 2 to 4; which comprises contacting one of said intermediates with an amidine of formula

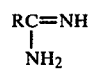

in the presence of reaction inert solvent and base; and a process for preparing a further intermediate, 1,2-dichloro-1-buten-3-one.

6 Claims, No Drawings

PROCESS FOR PREPARATION OF 4-ACETYL-2-SUBSTITUTED-IMIDAZOLES

BACKGROUND OF THE INVENTION

1. Field of the Invention

The invention relates to a novel process for preparation of 4-acetyl-2-substituted-imidazoles and intermediate 2-chloro-1-alkylthio-1-butene-3-one and 2-chloro-1,1-dialkoxy-3-butanones.

2. Description of the Prior Art

Methods for preparation of 4-acetyl-2-alkyl (or aralkyl)imidazoles and their utility as intermediates for preparation of 2-guanidino-4-imidazolylthiazole compounds, useful as antisecretory agents for treatment of peptic ulcers and other conditions caused or aggravated by gastric hyperacidity, are disclosed in U.S. Pat. No. 4,374,843, issued Feb. 22, 1983. These methods comprise irradiation of 1-acetyl-2-substituted imidazoles with ultraviolet light and reaction of a 2-halo-1-n-alkoxy-1-buten-3-one, e.g.

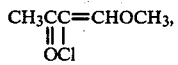

with an amidine or a salt thereof, in the presence of reaction inert solvent and base. The yields of 4-acetyl-2-methylimidazole by these two processes are low, on the order of 40–50 and 20–30%, respectively.

In copending application Ser. No. 445,787, filed Dec. 1, 1982, assigned to the same assignee, a process is disclosed for making 4-acetyl-2-methyl-imidazole (I, R=CH$_3$) from 2-methylimidazole-4-carboxaldehyde, in which the 1-position is protected e.g. by a benzyl group, by reaction with a methylmagnesium halide, e.g., methylmagnesium chloride, followed by deblocking and oxidation, or by oxidation, then deblocking.

The reaction of chloroacetyl chloride and aluminum chloride with a molar excess of 1,2-dichloroethylene has been reported by Catch et al., J. Chem. Soc. (London) 278 (1948) to afford chloromethyl 1,2,2-trichloroethyl ketone. McLamore et al., J. Org. Chem., 20, 109 (1955) have reported propionyl chloride to react with 1,2-dichloroethylene to provide ethyl 1,2,2-trichloroethyl ketone.

Methyl 1,2-dichlorovinyl ketone (IV) has been prepared by a three-step synthesis from 1,2-dichloro-1,3-butadiene by Petrov, J. Gen. Chem. (U.S.S.R.) 13, 230 (1943); Chem. Abstr., 38, 1467[4] (1944).

SUMMARY OF THE INVENTION

It has now been found that 4-acetyl 2-alkyl (or aralkyl) imidazoles of formula (I) can be prepared by the simplified method outlined below.

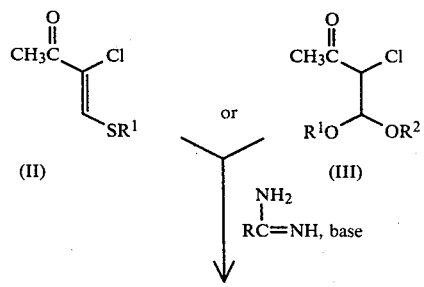

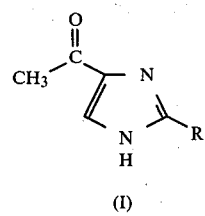

In the above compounds (I)–(III), R is (C$_1$–C$_6$)alkyl or (CH$_2$)$_n$Ar where Ar is phenyl or phenyl monosubstituted by Cl, Br, F, CH$_3$ or OCH$_3$ and n is 2 to 4;

R$^1$ and R$^2$ are each (C$_1$–C$_4$)alkyl, or when taken together they are (C$_2$–C$_4$)alkylene. This one step process of the invention is carried out in the presence of reaction inert solvent and base. A preferred range of temperature is from about 50° C. up to the reflux temperature of the solvent. An especially preferred temperature is from about 50° to 105° C. Particularly preferred reaction inert solvents are dioxane and t-butanol; an especially preferred base is sodium acetate.

A particularly preferred amidine for the process is acetamidine.

The invention further comprises the novel and valuable intermediate ketones of formula (II) and (III), as defined above. Of the intermediates, particularly preferred are those wherein R$^1$ and R$^2$ are each methyl or ethyl or taken together they form CH$_2$CH$_2$. Especially preferred compounds of formula (II) and (III) are those wherein R$^1$ and R$^2$ are each methyl.

The invention also provides a novel process for preparing the known compound (IV), 1,2-dichloro-1-buten-3-one (methyl 1,2-dichlorovinyl ketone), characterized in that equimolar amounts of acetyl chloride and anhydrous aluminum chloride are contacted in the presence of 1,2-dichloroethylene at a temperature of from 0° up to the reflux temperature of the mixture, i.e. about 60° C. and subsequent treatment with base, preferably aqueous sodium carbonate solution.

DETAILED DESCRIPTION OF THE INVENTION

The present invention relates to an improved method for preparing 4-acetyl-2-substituted imidazoles of formula (I) from the readily available and economical starting materials, acetyl chloride and 1,2-dichloroethylene, e.g. as shown below for the preferred case where R$^1$, R$^2$ and R are each methyl.

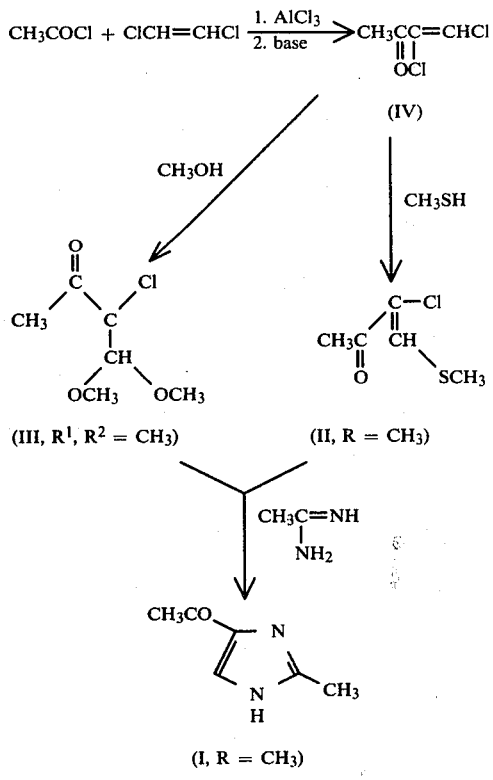

The reaction between the intermediate chloroketones (II) or (III) and amidine,

to form the desired imidazole of formula (I) is carried out in the presence of reaction inert solvent and a base.

By reaction inert solvent is meant one that does not adversely react to an appreciable extent with the reactants or products under the conditions employed, is capable of dissolving at least a substantial portion of the starting materials, and said solvent is one from which the desired product is readily recoverable by standard methods known in the art. Examples of such solvents are ethers such as tetrahydrofuran, dioxane, ethylene glycol dimethylether, diglyme (diethylene glycol dimethylether) and diisopropyl ether; alkanols such as methanol, n-propanol, isopropanol, sec-butanol, isobutanol, t-butanol, isoamyl alcohol, t-amyl alcohol, n-hexanol, 2-hexanol, 3-methyl-3-pentanol, cyclohexanol, ketones such as methylether ketone, diethyl ketone, cyclopentanone, cyclohexanone and chlorinated hydrocarbons such as methylene chloride, chloroform, 1,2-dichlorethane and the like. Particularly preferred reaction inert solvents are the ($C_3$–$C_6$)alkanols, tetrahydrofuran and dioxane, and especially preferred are dioxane and t-butanol.

The reactants of formula (II) or (III) and amidine (V) or its acid addition salt may be combined in approximately equimolar amounts in carrying out the process of the invention. It is usually preferred to employ a moderate excess of the amidine, e.g. from about 50–100 mole percent excess.

Preferably, the base is ordinarily employed in an amount from that which is sufficient to neutralize all acids generated during the reaction up to this amount plus a 50% excess based on the reactant of formula (II) or (III). Said acids generated include hydrochloric acid and other acids which may be combined with the amidine when said amidine employed is an acid addition salt, for example the amidine hydrochloride, amidine hydrobromide or amidine sulfate. Thus, e.g., if 1.0 mole of (III) and 1.5 moles of acetamidine hydrochloride are employed in the reaction, at least 2.5 equivalents, but not more than 3.0 equivalents, of base are ordinarily employed.

While a wide range of alkaline substances such as, e.g., the hydroxides, carbonates, acetates and phosphates of the alkali metal and alkaline earth metals; tertiary amines, quaternary amine hydroxides, basic ion exchange resins and the like can be employed as base in the above process, preferred bases for reasons of economy and efficiency include, for example, sodium acetate, sodium carbonate, sodium bicarbonate, potassium acetate, potassium carbonate, potassium bicarbonate, dipotassium hydrogen phosphate, disodium hydrogen phosphate, and the like. A particularly preferred base for this process is sodium acetate.

While the process of the invention to prepare the intermediate imidazoles of formula (I) may be carried out over a wide range of temperature, a preferred temperature is in the range of from about 50° C. up to the reflux temperature of the solvent. At these temperatures the reaction will be substantially completed in from a few hours to a few days. The product of formula (I) is then isolated, and purified if desired, by standard methods known in the art. For example, the solvent is evaporated to obtain the crude product which can be purified, e.g. by silica gel chromatography.

As mentioned above the invention also provides a process for preparing the intermediate (IV) by contacting equimolar amounts of acetyl chloride and anhydrous aluminum chloride in the presence of 1,2-dichloroethylene and subsequent treatment with base. While the reaction can be carried out in the presence of a reaction inert solvent, for example, any of the ethers, ketones or chlorinated hydrocarbon solvents mentioned above as solvents for preparation of imidazoles of formula (I), it is preferred to employ a solvent amount of the reactant 1,2-dichloroethylene. That is a sufficient excess of 1,2-dichloroethylene to allow it to serve both as reactant and solvent for the reactants and products, for example, from about a 2 to 10 molar excess, typically a 5 molar excess of 1,2-dichloroethylene, based on acetyl chloride. Typically, the acetyl chloride dissolved in 1,2-dichloroethylene is cooled to about 0° C. and the anhydrous aluminum chloride added in portions at 0°–25° C. The reaction mixture is then warmed, preferably to the reflux temperature (50°–60° C.) of the mixture for a period of about 4–24 hours. The mixture is then cooled, partitioned with water and the aqueous layer extracted with a water immiscible solvent, for example, methylene chloride, chloroform, ethyl ether or toluene. The combined organic layers are then treated with aqueous base to afford the desired product of formula (IV) which is isolated by standard methods.

While any of the above-mentioned bases, employed in the invention process to produce the imidazole compound (I) from intermediates (II) or (III) and an amidine (V), can also be used in this process with good result, the preferred base, for reasons of ease and economy, is aqueous sodium carbonate.

The invention processes are further illustrated in the following Examples. The following abbreviations are used for NMR peak multiplicity: s, singlet; d, doublet; t, triplet; m, multiplet.

EXAMPLE 1

1,2-Dichloro-1-buten-3-one

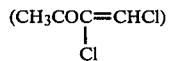

A mixture of 392 g (5.0 moles) acetyl chloride and 1817 g (18.75 moles) cis,trans-1,2-dichloroethylene under anhydrous conditions is cooled to 0° C. (acetonedry ice bath). To this was added in portions 734 g (5.5 moles) anhydrous aluminum chloride while maintaining the mixture below 25° C., the aluminum chloride being rinsed in with an additional 606 g (6.25 mole) 1,2-dichloroethylene. After the addition is completed, the cooling bath is removed and the mixture is heated at reflux (50°–60° C.) overnight. The cooled reaction mixture is poured onto ice, the organic layer separated and the aqueous layer is extracted with 3×500 ml methylene chloride. The combined organic layers are stirred vigorously, 450 g sodium chloride added and the small amount of water which separates is removed. The organic layer is filtered through diatomaceous earth (Celite) to remove the inorganic salts, then added to a solution of 748 g (6 moles) sodium carbonate monohydrate in sufficient water to make 2.5 liters of solution. The resulting mixture is stirred for 1.5 hours, the precipitated solid removed by filtration and washed with methylene chloride. The organic layer is separated, the aqueous portion extracted with 2×200 ml methylene chloride and the combined organic layers are dried (Na$_2$SO$_4$). The solvent is removed by evaporation in vacuo and the residual oil distilled to afford 517.5 g (74.5%) of product as a pale yellow liquid, B.P. 40°–52° C. at 8 mm. $^1$H-NMR (CDCl$_3$) ppm (delta): 2.50 (s, 3H), 7.55 (s, 1H).

EXAMPLE 2

2-Chloro-1,1-dimethoxy-3-butanone

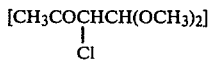

To a solution of 297 g (5.5 mole) sodium methoxide in 5 liters of methanol at 0° C., is added in a slow stream 695 g (5.0 mole) 1,2-dichloro-1-buten-3-one. After the addition is complete, the mixture is stirred at 0° C. for one hour, an additional 54 g (1.0 mole) sodium methoxide is added, and stirring continued at 0° C. for one hour. The mixture is allowed to stir at room temperature overnight, another g mole of sodium methoxide added and stirring continued for an hour. The mixture is filtered (filter aid) to remove salts, washing with fresh methanol. The filtrate is concentrated in vacuo to a slurry which is taken up in isopropyl ether and washed in turn with water, saturated sodium bicarbonate solution and brine, then dried over anhydrous magnesium sulfate. The extract is concentrated in vacuo to provide a residual oil which is distilled in vacuo to afford a main fraction of 628 g (75%) of product, B.P. 66°–75° C. at 8 mm. $^1$H-NMR (CDCl$_3$) ppm (delta): 2.33 (s, 3H), 3.43 (s, 3H), 3.47 (s, 3H), 4.23 (d, 1H), 4.63 (d, 1H).

EXAMPLE 3

2-Chloro-1,1-diethoxy-3-butanone

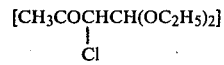

To a solution of 2.30 g of sodium metal in 180 ml ethanol, cooled in an ice-bath is added dropwise a solution of 13.90 g (0.10 mole) 1,2-dichloro-1-buten-3-one in 20 ml ethanol. The mixture is stirred for 2 hours, acidified with glacial acetic acid (4 ml) and the precipitated salt removed by filtration, washing with ethanol. The filtrate is concentrated in vacuo, the residue slurried in ethyl ether and filtered to remove salt. The ether is evaporated in vacuo and the residual oil is distilled to yield 12.49 g (64%) of the title compound, B.P. 52° C. at 1.5 torr. $^1$H-NMR (CDCl$_3$) ppm (delta): 1.17 (t, 3H), 1.22 (t, 3H), 2.30 (s, 3H), 3.63 (m, 4H), 4.18 (d, 1H), 4.68 (d, 1H).

EXAMPLE 4

2-(1-Chloro-2-oxopropyl)dioxolane

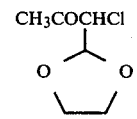

To a solution of 1.15 g (50 mmole) sodium metal in 50 ml ethylene glycol at 0° C. is added dropwise 6.95 g (50 mmole), 1,2-dichloro-1-buten-3-one and the resulting mixture is stirred at room temperature for two hours. The mixture is poured into 100 ml water, extracted with ethyl ether and the extracts washed with water, brine and dried (MgSO$_4$). Evaporation of ether affords a brown oil which is distilled in vacuo to provide 2.36 g (29%) of the desired cyclic acetal, B.P. 92°–94° C. at 9 torr. $^1$H-NMR (CDCl$_3$) ppm (delta): 2.37 (s, 3H), 4.03 (m, 4H), 4.27 (d, 1H), 5.28 (d, 1H).

Repeating the procedures of Examples 2–4 with the appropriate alcohol or glycol provides compounds of the formula below in like manner.

$$CH_3COCH-CH\begin{matrix}\diagup OR^1 \\ \diagdown OR^2\end{matrix}$$
$$\quad\;\;|\\ \quad\;Cl$$

| R$^1$ | R$^2$ | R$^1$ + R$^2$ |
|---|---|---|
| n-propyl | n-propyl | (CH$_2$)$_3$ |
| isopropyl | isopropyl | CH$_2$CH(CH$_3$) |
| n-butyl | n-butyl | (CH$_2$)$_4$ |
| isobutyl | isobutyl | CH$_2$CH$_2$CH(CH$_3$) |

EXAMPLE 5

2-Chloro-1-methylthio-1-buten-3-one

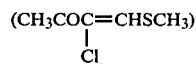

To a solution of 6.95 g (50 mmole) 1,2-dichloro-1-buten-3-one in 50 ml ethyl ether is added 2.41 g (50 mmole) methyl mercaptan. To this is added dropwise 5.06 g (50 mmole) triethylamine at such a rate as to maintain a gentle reflux. After standing for two hours, the solid is broken up, additional ether is added to facilitate stirring and an additional 2 ml triethylamine is added. The mixture is stirred for another hour, filtered to remove triethylamine hydrochloride, washing with ether. Evaporation of solvent affords the crude product as an orange oil which is distilled in vacuo to give 5.3 g (74%) of yellow liquid, B.P. 108°–110° C. at 10 mm. Mass spectrum (m/e) 150 (molecular ion). $^1$H-NMR (CDCl$_3$) ppm (delta): 2.37 (s, 3H), 2.53 (s, 3H), 7.78 (s, 1H).

EXAMPLE 6

2-Chloro-1-t-butylthio-1-buten-3-one

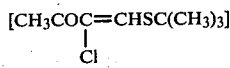

To a mixture of 20.85 g (0.15 mole) 1,2-dichloro-1-buten-3-one and 13.53 g (0.15 mole) t-butylmercaptan in 300 ml ethyl ether, cooled to 5° C. is added dropwise 15.18 g (0.15 mole) triethylamine in 50 ml ether. After stirring at room temperature for 18 hours the mixture is heated at reflux for 2 days. The resulting mixture is washed with water, brine and the organic layer dried over magnesium sulfate. Evaporation of ether affords a brown oil which is distilled in vacuo to yield 17.56 g of product as a light yellow liquid, B.P. 75° (0.1 mm) which crystallized upon standing, M.P. 73° C. Mass spectrum (m/e) 192 (molecular ion), 138, 136.

Use of the appropriate $C_2$–$C_4$ mercaptan ($R^1$SH) in the above procedure affords the compounds of the formula below

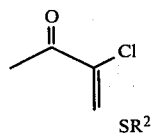

where $R^1$ is ethyl, n-propyl, isopropyl, n-butyl or sec-butyl.

EXAMPLE 7

4-Acetyl-2-methylimidazole

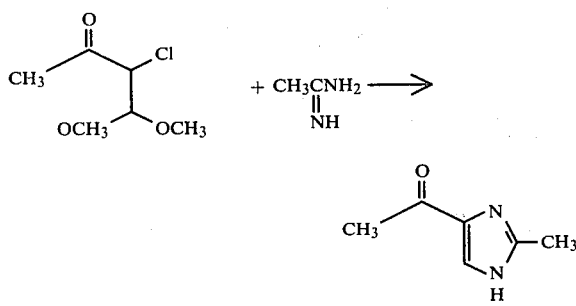

A. In 500 ml of dioxane are added 83.5 g (0.50 mole) 2-chloro-1,1-dimethoxy-3-butanone, 94.5 g (1.0 mole) acetamidine hydrochloride and 123 g (1.5 mole) sodium acetate and the mixture is heated at reflux overnight. The cooled reaction mixture is filtered through a silica gel pad on a sintered glass filter funnel, washing with 3500 ml of dioxane. The filtrate and washings are combined and evaporated in vacuo to provide a residual oil which is purified by chromatography on a silica gel column (600 g), eluting with ethyl acetate. Fractions of 200 ml each are collected. After 16 fractions the elution is with 95:5 ethyl acetate/methanol. Fractions 18–35 are combined and the solvent evaporated in vacuo to afford 28.82 g (46.4%) of the desired product. Recrystallization from 1:1 ethyl acetate/isopropyl ether yields 19.27 g (31%) of crystals, M.P. 132°–133° C. Another 4.24 g (6.8%) was obtained by reworking the mother liquor. $^1$H-NMR (CD$_3$OD) ppm (delta): 2.40 (s, 3H), 2.43 (s, 3H), 7.68 (s, 1H).

B. A mixture of 1.66 g (10 mmole) 2-chloro-1,1-dimethoxy-3-butanone, 1.43 g (15 mmole) acetamidine hydrochloride and 2.05 g (25 mmole) sodium acetate in 50 ml dioxane is heated at reflux for 24 hours. The dioxane is evaporated in vacuo and the residual oil is flash chromatographed on silica gel (40:60 ethyl acetate/hexane, 40 mm) to obtain three fractions. The third fraction, a white solid (1.121 g) was rechromatographed (40 mm, acetone) to afford 933 mg (75.1%) of product as white solid which is pure as judged by its NMR spectrum in CDCl$_3$ and by TLC on silica gel (one spot, 1:9 methanol/chloroform).

EXAMPLE 8

4-Acetyl-2-methylimidazole

A. To 100 ml of tertiary butyl alcohol is added 1.95 g (10.0 mmole) 2-chloro-1,1-diethoxy-3-butanone, 2.36 g (20 mmole) acetamidine acetate and 0.82 g (10 mmole) sodium acetate and the mixture is heated at reflux for 48 hours. The cooled reaction mixture is concentrated in vacuo to a syrup and the crude product purified by chromatography on a silica gel column, eluting with 95:5 chloroform/methanol. The product containing fractions are combined and the solvent evaporated to afford 479 mg (39%) of product as a white powder, M.P. 130°–132° C.

B. A mixture of 1.64 g (10 mmole) 2-(1-chloro-2-oxopropyl)dioxolane, 1.89 g (20 mmole) acetamidine hydrochloride, 2.46 g (30 mmole) sodium acetate and 20 ml t-butanol is heated at reflux for 24 hours and the product isolated as in Part A.

EXAMPLE 9

4-Acetyl-2-n-hexylimidazole

To 100 ml dioxane is added 4.94 g (30 mmole) heptanamidine, 3.33 g (20 mmole) 2-chloro-1,1-dimethoxy-3-butanone and 4.10 g (50 mmole) sodium acetate and the mixture is heated at reflux for five hours. The mixture is cooled in ice, precipitated salts removed by filtration, washing with dioxane. The filtrate and washings are concentrated in vacuo to an oil. The oil is taken up in 100 ml ethyl acetate and extracted with 3×20 ml 1N hydrochloric acid. The aqueous extracts are washed with ethyl acetate, made alkaline with solid sodium carbonate and extracted with 3×25 ml chloroform. The chloroform layers are dried (Na$_2$CO$_3$) and solvent evaporated to give 2.16 g (55%) of tan solid. Recrystallization from cyclohexane (100 ml) yields 1.16 g (29.8%) of colorless solid, M.P. 103°–106° C.

Repeating the above procedure with 0.20 mole of heptanamidine, 0.15 mole 2-chloro-1,1-dimethoxy-3-butanone, 0.35 mole sodium acetate in 400 ml dioxane by refluxing for six hours, allowing to stand overnight at room temperature and work-up as above, affords a 42% yield of pure product, M.P. 104°–106° C. and 26% of impure product. For the pure sample: $^1$H-NMR (CDCl$_3$) ppm (delta): 0.85 (t, 3H), 1.28 (m, 7H), 1.75 (m, 2H), 2.52 (s, 3H), 2.83 (t, 2H), 7.72 (s, 1H).

EXAMPLE 10

Repeating the procedure of the previous example with the indicated starting materials, provides the desired products of formula (I) in like manner.

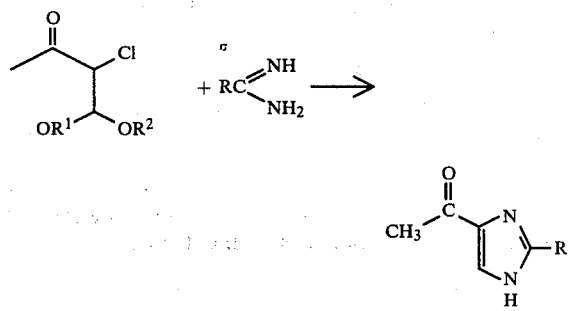

wherein R$^1$ and R$^2$ are taken separately:

| R$^1$ | R$^2$ | R |
|---|---|---|
| CH$_3$ | CH$_3$ | C$_2$H$_5$ |
| C$_2$H$_5$ | C$_2$H$_5$ | C$_2$H$_5$ |
| n-C$_3$H$_7$ | n-C$_3$H$_7$ | n-C$_3$H$_7$ |
| i-C$_3$H$_7$ | i-C$_3$H$_7$ | n-C$_4$H$_9$ |
| n-C$_4$H$_9$ | n-C$_4$H$_9$ | (CH$_3$)$_2$CHCH$_2$CH$_2$ |
| sec-C$_4$H$_9$ | sec-C$_4$H$_9$ | n-C$_6$H$_{13}$ |
| CH$_3$ | CH$_3$ | C$_6$H$_5$CH$_2$CH$_2$ |
| C$_2$H$_5$ | C$_2$H$_5$ | 4-ClC$_6$H$_4$(CH$_2$)$_3$ |
| CH$_3$ | CH$_3$ | 3-CH$_3$C$_6$H$_4$(CH$_2$)$_4$ | where R$^1$ and R$^2$ are taken together:

| R$^1$ + R$^2$ | R |
|---|---|
| CH$_2$CH$_2$ | C$_2$H$_5$ |
| CH$_2$CH$_2$CH$_2$ | CH$_3$ |
| CH(CH$_3$)CH$_2$ | (CH$_3$)$_2$CHCH$_2$ |
| CH$_3$CHCHCH$_3$ | 2-BrC$_6$H$_4$(CH$_2$)$_4$ |
| (CH$_2$)$_4$ | 3-FC$_6$H$_4$(CH$_2$)$_4$ |
| CH$_2$CH$_2$ | 4-CH$_3$OC$_6$H$_4$(CH$_2$)$_2$ |

EXAMPLE 11

4-Acetyl-2-methylimidazole

To 50 ml of dioxane is added 1.51 g (10 mmole) 2-chloro-1-methylthio-1-buten-3-one, 1.43 g (15 mmole) acetamidine hydrochloride and 2.05 g (25 mmole) sodium acetate and the mixture is heated at reflux for 24 hours. The reaction mixture is concentrated in vacuo and the residue is flash chromatographed on silica gel (40 mm, 1:19 methanol/chloroform). The fractions containing the product are combined and rechromatographed (40 mm, acetone) to afford 576 mg of white solid title compound. This is further purified by chromatography to give 348 mg (28%) of pure imidazole.

Rechromatographing the mother liquors gives 478 mg (31.7%) of starting material (2-chloro-1-methylthio-1-buten-3-one) and 320 mg (21%) of 2,4-dimethyl-5-methylthiopyrimidine. Mass spectrum (m/e): 154 (molecular ion). M.P. 49°–50.5° C.

In like manner the remaining 2-chloro-1-alkylthio-1-buten-3-ones provided in Example 6 are employed as starting material in the above procedure to provide the title compound.

EXAMPLE 12

4-Bromoacetyl-2-methylimidazole Hydrobromide 2.40 g (19.3 mmol) of 4-acetyl-2-methylimidazole was dissolved in 30 ml of 48% hydrogen bromide. To the stirred solution at 25° was added over a 5 minute period 3.36 g (21 mmol) of bromine dissolved in 5 ml 48% hydrogen bromide. The reaction was heated to 70° for 2.5 hours and then concentrated in vacuo to a dark oil. A mixture of isopropyl alcohol/ether was added and trituration of the oil gave a solid. This was collected by filtration and washed with ether to give 2.8 g (51%) of the title product, M.P. 181° (dec.); nmr (DMSO-d$_6$) (delta): 8.71 (s, 1H); 4.77 (s, 2H); 2.63 (s, 3H).

EXAMPLE 13

2-Guanidino-4-(2-methyl-4-imidazolyl)thiazole Hydrobromide 2.8 g (9.86 mmol) of 4-bromo-acetyl-2-methylimidazole hydrobromide was dissolved in 10 ml water. Saturated sodium bicarbonate solution was added to pH 10 and the resultant solid was collected by filtration and washed with 15 ml water. The dried free base was heated at reflux in 50 ml acetone. To the refluxing clear acetone solution was added 1.2 g (9.86 mmol) of amidinothiourea. Solution occurred immediately and within a minute a solid began to form. After one hour reflux the slurry was cooled and the solid was collected by filtration and was washed with acetone followed by ether to give 2.37 g (79%) of the title compound, M.P. 158° (dec.); nmr (DMSO-d$_6$) (delta): 7.71 (s shoulder on broad s, 1H); 7.56 (broad s, 4H); 4.32 (s, 1H); 2.51 (s, 3H).

EXAMPLE 14

Employing the 4-acetyl-2-R-substituted imidazoles provided in Example 10 as starting material in the procedure of Example 12, and reacting the resulting 4-bromoacetyl-2-R-imidazole with amidinothiourea by the procedure of Example 13, similarly provides compounds of the formula below where R is as defined in Example 10.

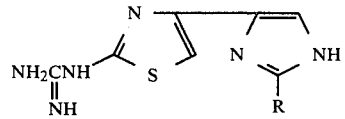

I claim:

1. A process for preparation of a compound of the formula

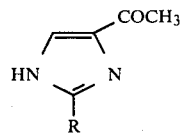

wherein R is (C$_1$–C$_6$)alkyl or (CH$_2$)$_n$Ar where Ar is phenyl or phenyl monosubstituted by Cl, Br, F, CH$_3$ or OCH$_3$ and n is 2 to 4; which comprises contacting a compound of the formula

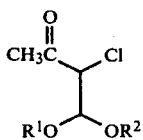

wherein $R^1$ and $R^2$ are each $(C_1-C_4)$alkyl or when taken together $R^1$ and $R^2$ are $(C_2-C_4)$alkylene with an amidine of the formula

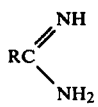

in the presence of reaction-inert solvent and a base at a temperature of from 50° C. up to the reflux temperature of the solvent.

2. A process according to claim 1 wherein $R^1$ and $R^2$ are each methyl or ethyl or taken together they form $CH_2CH_2$.

3. A process according to claim 2 wherein R, $R^1$ and $R^2$ are each methyl.

4. A process according to claim 1 wherein said reaction inert solvent is tetrahydrofuran, dioxane, or a $(C_3-C_6)$alkanol and said base is sodium acetate, sodium carbonate, sodium bicarbonate, disodium hydrogen phosphate, potassium acetate, potassium carbonate, potassium bicarbonate or dipotassium hydrogen phosphate.

5. A process according to claim 4 wherein said solvent is dioxane or t-butanol, said base is sodium acetate and said reaction is carried out at the reflux temperature.

6. The process according to claim 3 wherein said solvent is dioxane, said base is sodium acetate and said reaction is carried out at the reflux temperature.

* * * * *